(12) United States Patent
Stark

(10) Patent No.: US 6,560,310 B2
(45) Date of Patent: May 6, 2003

(54) APPARATUS FOR MAMMOGRAPHY

(75) Inventor: Iain Stark, Manotick (CA)

(73) Assignee: IS2 Research Inc., Nepean (CA)

( * ) Notice: Subject to any disclaimer, the term of this patent is extended or adjusted under 35 U.S.C. 154(b) by 0 days.

(21) Appl. No.: 09/871,830

(22) Filed: Jun. 1, 2001

(65) Prior Publication Data

US 2002/0057758 A1 May 16, 2002

(30) Foreign Application Priority Data

Nov. 16, 2000 (CA) .............................................. 2326026

(51) Int. Cl.$^7$ ................................................. A61B 6/04
(52) U.S. Cl. .......................... 378/37; 378/209; 5/601; 250/366; 250/363.1
(58) Field of Search ...................... 378/37, 208, 209, 378/68; 5/601, 621; 250/366, 363.08, 363.1, 363.02

(56) References Cited

U.S. PATENT DOCUMENTS

| | | | |
|---|---|---|---|
| 3,973,126 A | * | 8/1976 | Redington et al. .......... 378/156 |
| 4,675,526 A | * | 6/1987 | Rogers et al. ........... 250/363.5 |
| 5,252,830 A | | 10/1993 | Weinberg |
| 5,323,006 A | | 6/1994 | Thompson et al. |
| 5,519,221 A | | 5/1996 | Weinberg |
| 5,609,152 A | * | 3/1997 | Pellegrino et al. ........ 128/653.1 |
| 5,803,913 A | * | 9/1998 | Khalkhali et al. ........... 600/407 |
| 5,965,891 A | | 10/1999 | Weinberg |
| 6,194,725 B1 | * | 2/2001 | Colsher et al. ........ 250/363.05 |
| 6,229,145 B1 | | 5/2001 | Weinberg |
| 6,298,114 B1 | * | 10/2001 | Yoda ........................... 378/37 |

* cited by examiner

Primary Examiner—Drew A. Dunn
Assistant Examiner—Elizabeth Gemmell
(74) Attorney, Agent, or Firm—Pearne & Gordon LLP

(57) ABSTRACT

An apparatus for mammography is disclosed. The apparatus comprises (a) a bed structure having a patient platform on which a patient lies face down, the patient platform having at least one opening through which the breast of the patient hangs down, (b) a mechanism for holding the breast hanging down through the opening, and (c) a camera for taking a mammographic image of the breast held by the mechanism. The camera includes two scintillation cameras fixed relative to each other in the form of V-shape to accommodate both breasts of the patient simultaneously. The breast holding mechanism includes a breast container for gently accommodating the breast of the patient without causing any pain. The patient platform can rotate, together with the breast container, relative to the camera for three-dimensional imaging.

40 Claims, 6 Drawing Sheets

APPARATUS FOR MAMMOGRAPHY

FIELD OF THE INVENTION

The present invention generally relates to an apparatus for mammography, more particularly relates to a combination of a bed structure for supporting a patient, a breast holding mechanism for keep the breasts of the patient in position during mammography, and a camera for taking mammograms from the breasts.

BACKGROUND OF THE INVENTION

Research shows that breast cancer has reached epidemic proportions worldwide. It is the leading cause of death among U.S. women aged 15 to 54. It takes about 9 years before breast cancer cells are visible on a mammogram. Cancerous cells can spread to other parts of the body including the brain. The average five-year survival rate for patients where breast cancer is detected early is 96%. When breast cancer is detected late, the five-year survival rate drops to is 20%. Therefore, early stage detection is critical for improving chances for survival. However, in the early stage when breast cancer is most treatable, it typically produces no symptoms. Due to the limitations of diagnostic technology, the most important physical symptom of breast cancer is still a painless mass. Statistics and data about breast cancer support the fact that early detection is critical.

To date, x-ray mammography is the most effective tool for breast cancer detection, but it suffers from many problems as follows:

It can not tell if abnormalities are cancerous or benign. 10% of patients with breast cancer present with normal mammograms.

Cancer is correctly predicted only 10% to 40% of the time. 60% of biopsies show no cancer and are therefore unnecessary.

It is generally unsuccessful with dense breast tissue (found in 40% of screening aged women).

Breast ultrasound has been used with limited success. Several attempts have been made to apply scintillation cameras to the mammography. However, none of the current methods are expected to be satisfactorily successful for early detection and accurate location of breast cancer or tumour.

Accordingly, there is a need to solve the problems noted above and also a need for an innovative approach to advance the current technologies of mammography.

SUMMARY OF THE INVENTION

According to one aspect of the invention, there is provided an apparatus for mammography. An apparatus for mammography (a) a bed structure having a patient platform on which a patient lies face down, the patient platform having at least one opening through which the breasts of the patient hang down when in use, (b) a mechanism for holding the breasts which extend down through the opening in selected substantially fixed relation relative to the platform, the mechanism being adapted to accommodate the breasts without substantially distorting the inherent shapes of the downwardly extending breasts, and (c) a camera for providing a mammographic image of the breasts as they are being held by the mechanism.

The mechanism includes a pair of breast containers for accommodating the breasts while maintaining substantially the shape of the breasts in the field of view of the camera.

The camera is adapted to receive radiant energy from the patient breasts after the patient has been administered with a radiopharmaceutical substance, while substantially reducing the amount of radiation received by the camera from the remainder of the patient's body.

The breast containers has the shape of an inverted half-cone sectioned vertically through the vertex thereof, preferably the shape of an inverted truncated half-cone sectioned vertically through the vertex thereof. The breast containers can have the shape of a flaring chute. The breast holding mechanism further includes a plurality of pushing pads for further holding the breasts and fitting them into the breast containers. The breast container has a plurality of perforations so that a surgical tool or a biopsy gun is accessible to the breast through the perforations The breast holding mechanism is slidably and detachably attached to the bed structure. Therefore, the distance between the breast holding mechanism and the bed structure is adjusted depending on the size of the breasts of patients.

The bed structure further comprises means for rotating the patient platform to both sides thereof about an axis normal to the platform passing through a region intermediate the pair of breast containers. The patient platform is rotated about a vertical axis passing through the cleavage area between of both breasts of the patient when lying face down on the patient platform.

The bed structure is provided with an aperture for accommodating the face of the patient. The bed structure is provided with means, under the aperture, for distracting the patient from mammography. The distracting means includes an artistic picture.

The camera comprises a first scintillation camera having a first collimator, the first collimator defining a first camera surface, a second scintillation camera having a second collimnator, the second collimator defining a second camera surface, wherein the first ant second scintillation cameras are fixed relative to each other such that the first and second camera surfaces together form a "V" shape. The breast holding mechanism is located within the confines of the "V" shape, thereby allowing mammographic images of both breasts of the patient to be provided simultaneously. The camera can also have access to the armpit area of the patient such that the axillary lymph nodes can be viewed by the camera.

The apparatus for mammography further comprises a radiation source for determining the relative position of the breast to the camera. Also, the apparatus further comprises means for shielding radiation from each other breast. The shielding means is located to prevent a cross-talk between the first and second scintillation cameras.

The collimator holes of the collimators are slanted relative to the camera surfaces such that radiation from other body parts of the patient is substantially prevented from being received by the camera. The slant collimator holes are parallel to the transversal direction of the patient platform, and thus substantially parallel to the chest wall of the patient when lying face down an the patient platform. For example, the first and second camera surfaces are at about 90 degrees with each other, and the collimator holes are at about 45 degrees with the camera surfaces.

According to another aspect of the invention, there is provided a patient supporting structure for using in the examination and treatment of women's breast. The patient supporting structure comprises the bed structure and the breast holding mechanism, which are noted above.

A further understanding of the other features, aspects, and advantages of the present invention will be realized by reference to the following description, appended claims, and accompanying drawings.

BRIEF DESCRIPTION OF THE DRAWINGS

Embodiments of the invention will now be described with reference to the accompanying drawings, in which.

DETAILED DESCRIPTION OF THE PREFERRED EMBODIMENT(S)

Figure 1:
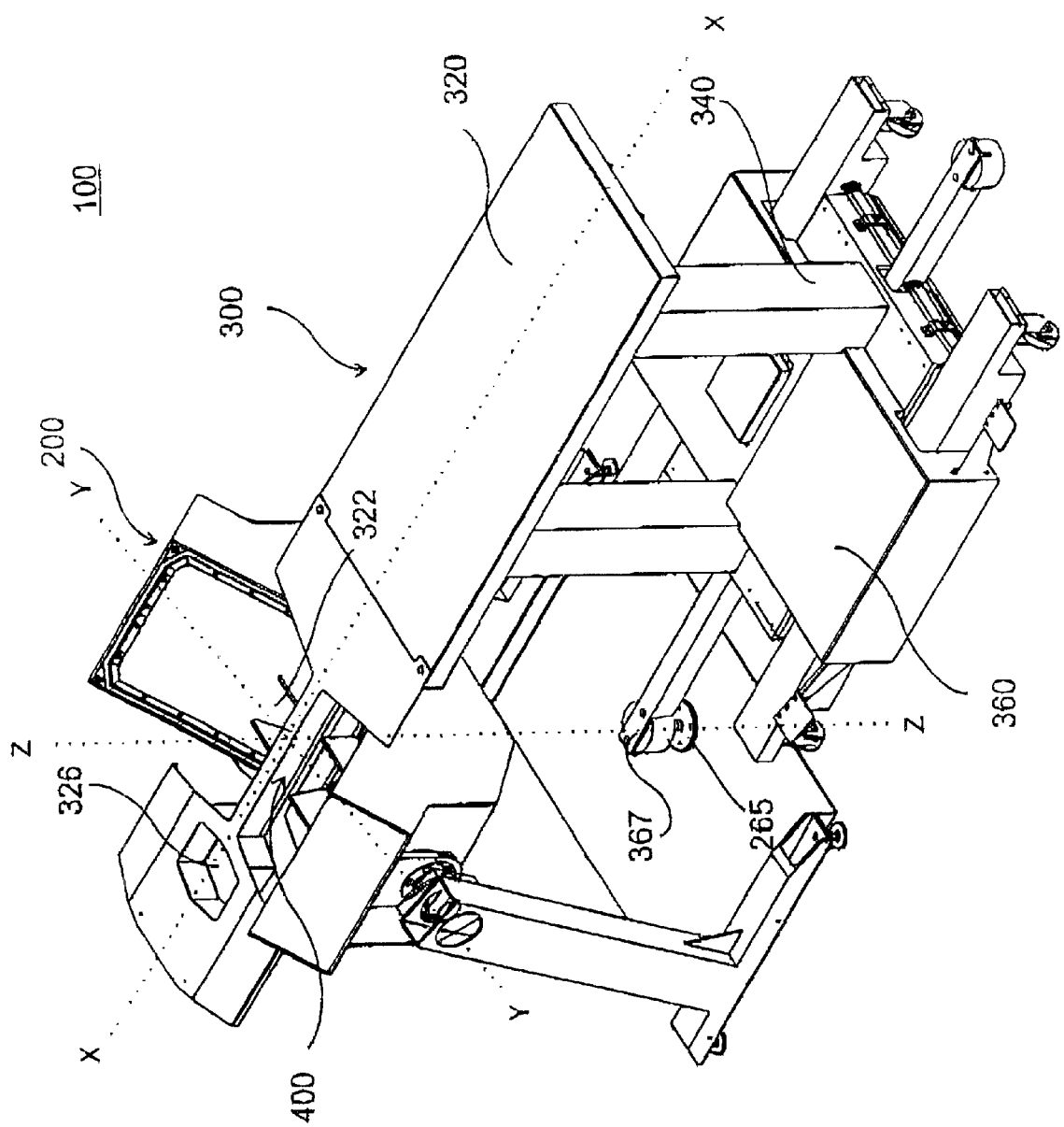
FIG. 1 is a perspective view of an apparatus for mammography according to one embodiment of the invention.
Figure 2:
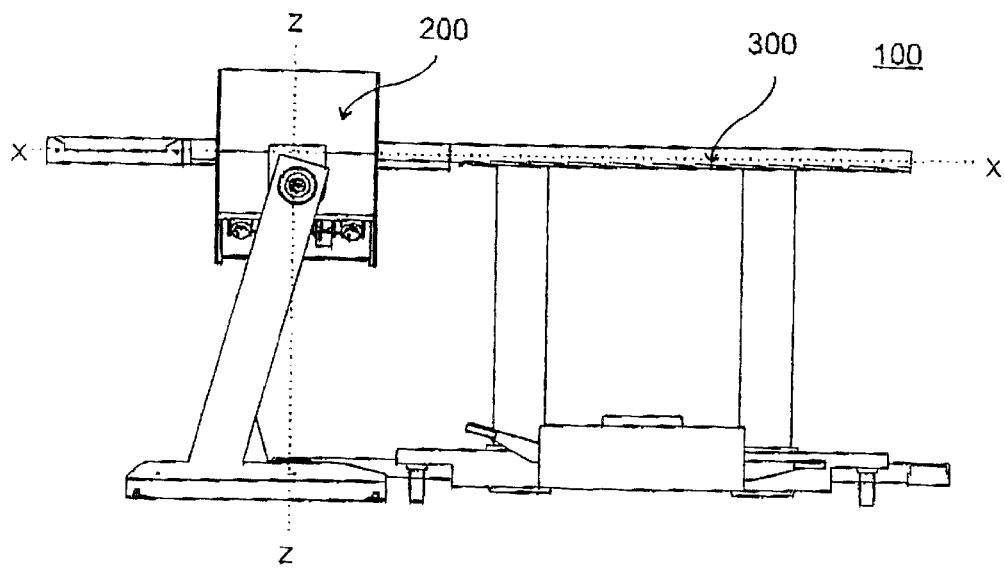
FIG. 2 is a side view of the apparatus of FIG. 1.
Figure 3:
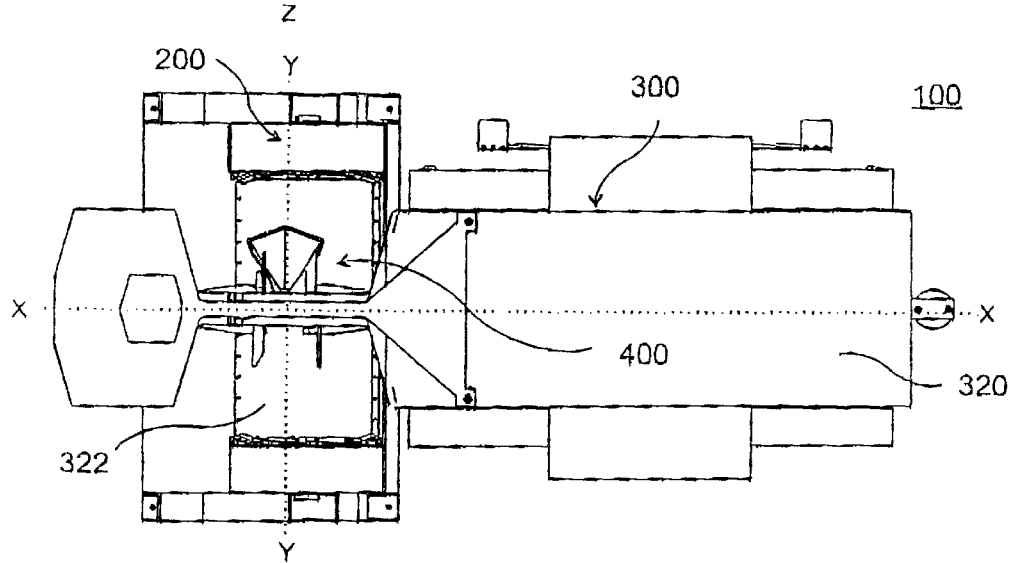
FIG. 3 is a top view of the apparatus of FIG. 1.
Figure 4:
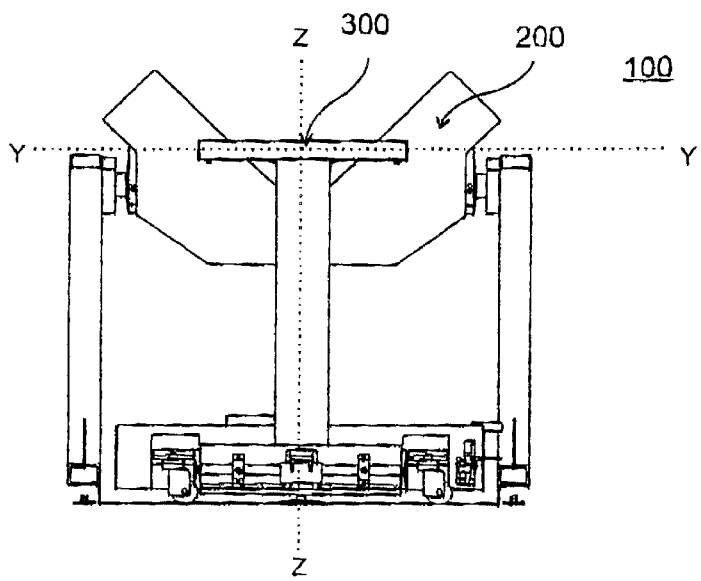
FIG. 4 is a fontal view of the apparatus of FIG. 1.

In FIG. 1, there is shown an apparatus for mammography according to one embodiment of the invention, which is generally denoted by a reference numeral 100. FIGS. 2 to 4 show a side view and a top view and a front view respectively of the apparatus of FIG. 1. Referring to FIGS. 1 to 4, the apparatus 100 of the invention generally comprises a camera 200, a bed structure 300, and a breast holding mechanism 400. The bed structure 300 is provided with a patient platform 320 on which a patient ties face down. The patient platform 320 includes an opening 322 through which the breasts of the patient hang down when she lies face down thereon. The breast holding mechanism 400 gently holds the breasts hanging down through the opening 322 without causing any pain to the patient. The camera 200 takes mammographic images of the beast contained in the breast holding mechanism. In this embodiment, the camera 200 has a V-shape as shown in the front view of FIG. 4, so that it can accommodate both breasts of the patient simultaneously. Further details will be described below.

Figure 5:
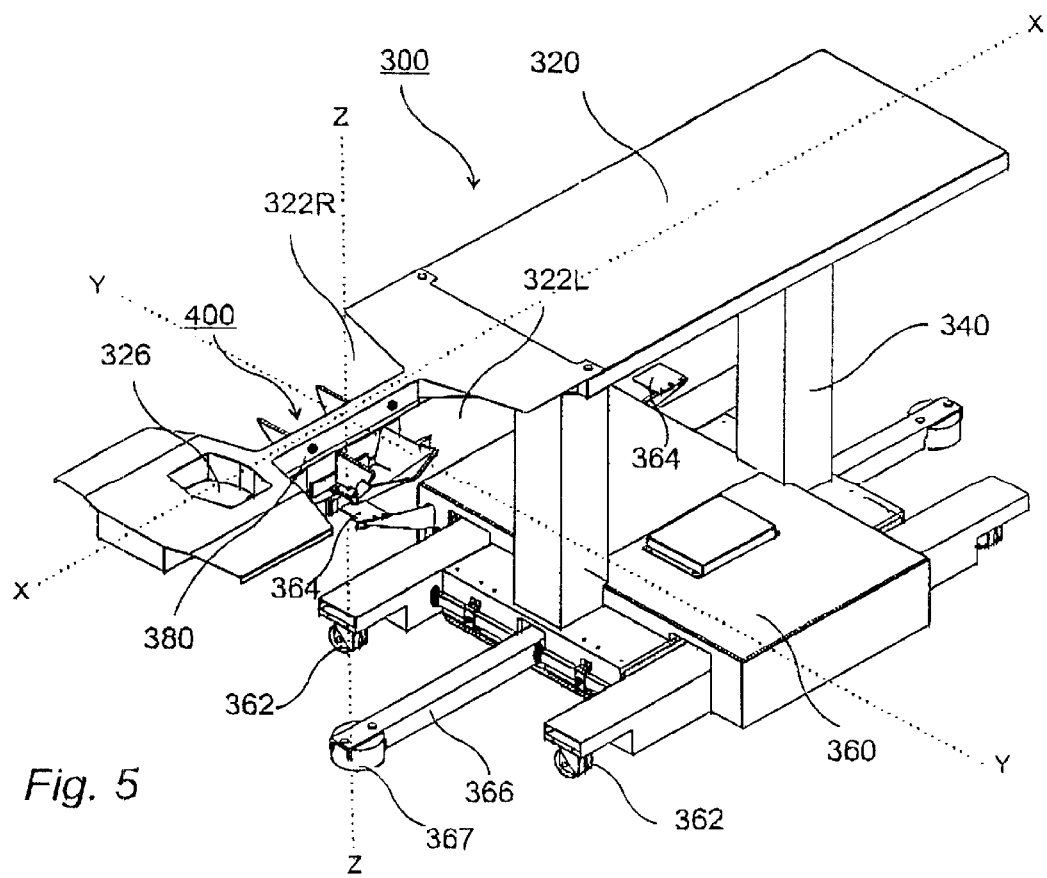
FIG. 5 is a perspective view of the bed structure and breast holding mechanism in the apparatus of FIG. 1.

FIG. 5 shows a perspective view of the bed structure 300 and the breast holding mechanism 400 of the apparatus 100. Referring to FIG. 5, the bed structure 300 comprises a patient platform 320 on which the patient lies face down, a pair of platform support legs 340, and a driving mechanism 360 for adjusting the bed structure 300 to a suitable position and height for mammography or other suitable treatments.

Figure 6:
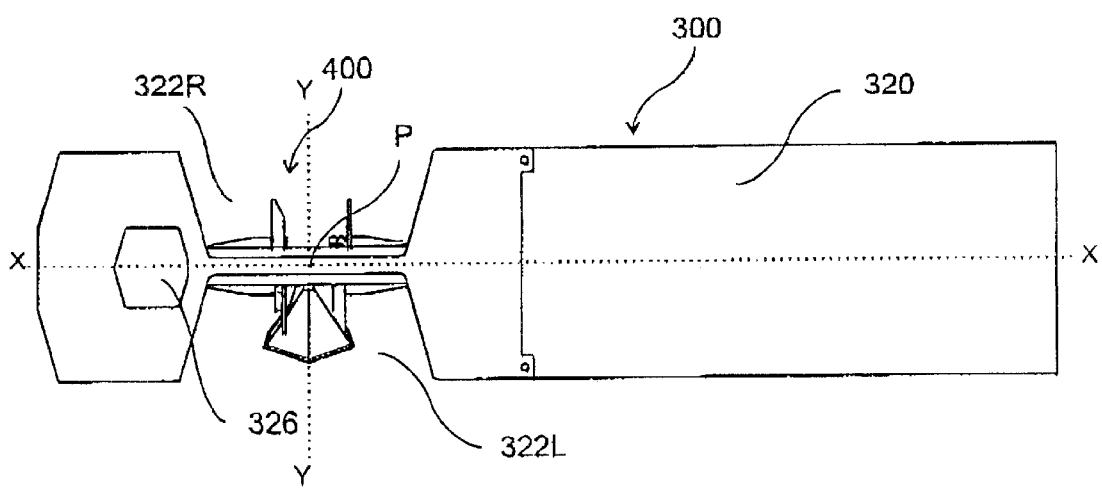
FIG. 6 is a top view showing the structure of the patient platform in the bed structure of FIG. 5.

FIG. 6 illustrates the configuration of the patient bed 320 of the bed structure 300. Referring to FIGS. 5 and 6, various aspects of the patient bed 320 will be described. As shown in FIGS. 5 and 6, the patient platform 320 is provided with the opening 322, which in this embodiment, comprises a pair of openings 322L and 322R for both breasts, through which the breasts of the patient comfortably hang down when she lies face down on the platform 320. For the convenience of description, the opening 322L is for the left breast, and the opening 322R for the right one. The area between the openings 322L and 322R supports the cleavage portion between both breasts of the patient. In this embodiment, each opening is formed by cutting out part of the patient platform 320. Each downwardly hanging breast is gently held by the breast holding mechanism 400 provided below the openings 322L and 322R, which will be described hereafter in greater detail.

The patient platform 320 further includes an aperture 326 in the location corresponding to the head of the patient when she lies on the platform. The aperture 326 serves to accommodate the face of the patient without the necessity of turning her head when she lies face down, and thus it helps her stay as still as possible during mammography or any treatment for her breasts. It takes time to carry out mammography and, if needed, subsequent treatments, including surgery and biopsy. Although not shown in the drawings, a TV screen or a computer screen can be provided under the aperture 326 for providing some entertainment, such as an artistic picture, an electronic Magazine, a movie and so forth. Therefore, the patient is distracted from the mammography procedure, which also helps her to remain still throughout the procedure Although a pair of platform support legs 340 is illustrated in this embodiment, four support legs can be provided. As shown in FIG. 5, the driving mechanism 360, to which the support legs 340 are firmly attached, includes four floor-engaging casters 362 rotatably fixed thereto at the four corners thereof, so that the bed structure 300 can move over the floor of the room, in which the apparatus is located, to any suitable location for taking mammograms. Further, a lifting paddle 364 is provided to enable the technician operating the apparatus to adjust the height of the patient platform to any comfortable height for taking mammograms or treating the patient. As is well-known to those skilled in the art, all these adjustments can be automated and electrically driven.

The bed structure 300 further includes a mechanism 366 for rotating the patient platform 320 about a vertical axis when taking three-dimensional images of the breasts, which mechanism will be detailed hereafter, in conjunction with the description of the camera 200 of the apparatus 100.

Figure 7:
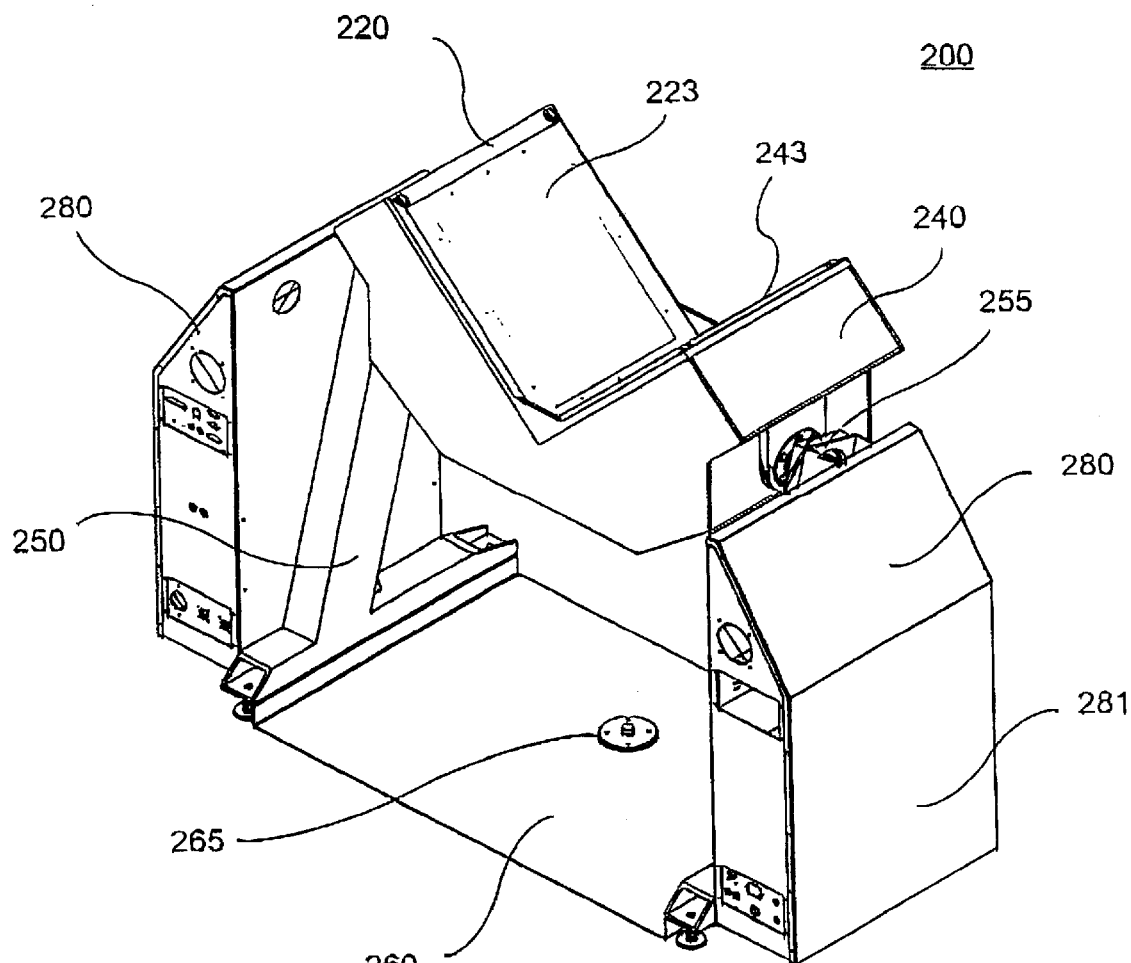
FIG. 7 is a perspective view of the camera in the apparatus of FIG. 1.

FIG. 7 is a perspective view of the camera 200 for taking images of the breast. In this embodiment, the camera 200 comprises a scintillation camera, although it can be an X-ray camera suitable for taking mammograms. As illustrated in FIG. 7, the camera 100 comprises a first scintillation camera 220 and a second scintillation camera 240, each of which will be detailed hereafter by reference to FIG. 11. The camera 200 includes a pair of support legs 250 extending upwardly from a support plate 260 extending between the pair of support legs 250, the support plate being disposed on the floor. The first and second scintillation cameras 220 and 240 are pivotably supported to the support legs 250 by a mounting structure 255 so that the camera angle relative the patient can be adjusted. Also, the camera 200 can be provided with a computer 280 (located in housings 281, disposed in close proximity to the camera support legs 250) for image processing, and a monitor (not shown) for displaying the images processed by the computer.

Figure 11:
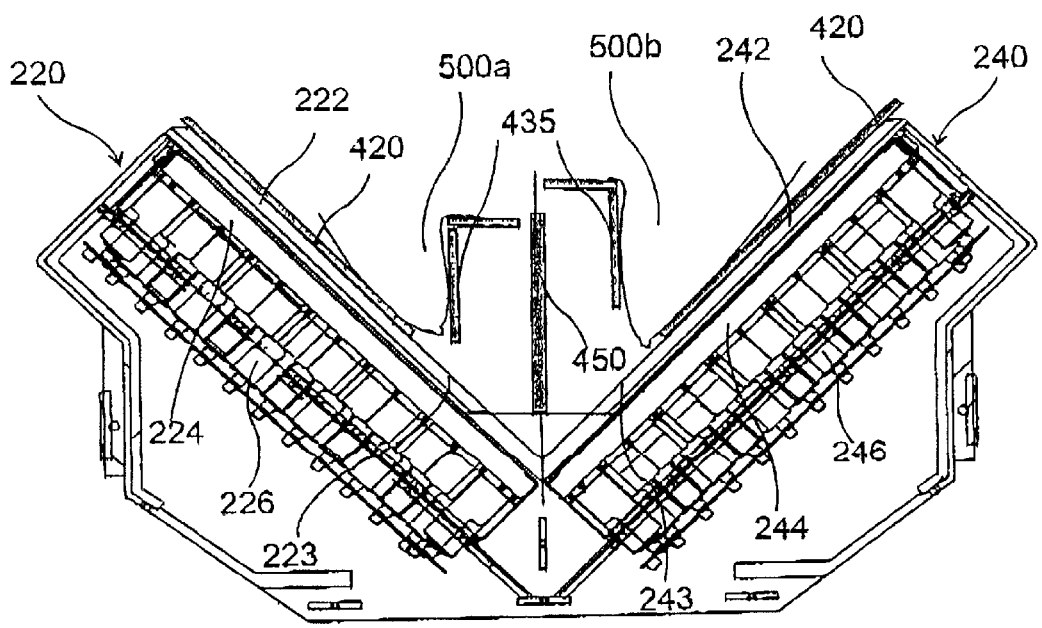
FIG. 11 is a sectional view of the camera and the breast holding mechanism, in which the breasts of a patient is contained.
Figure 12:
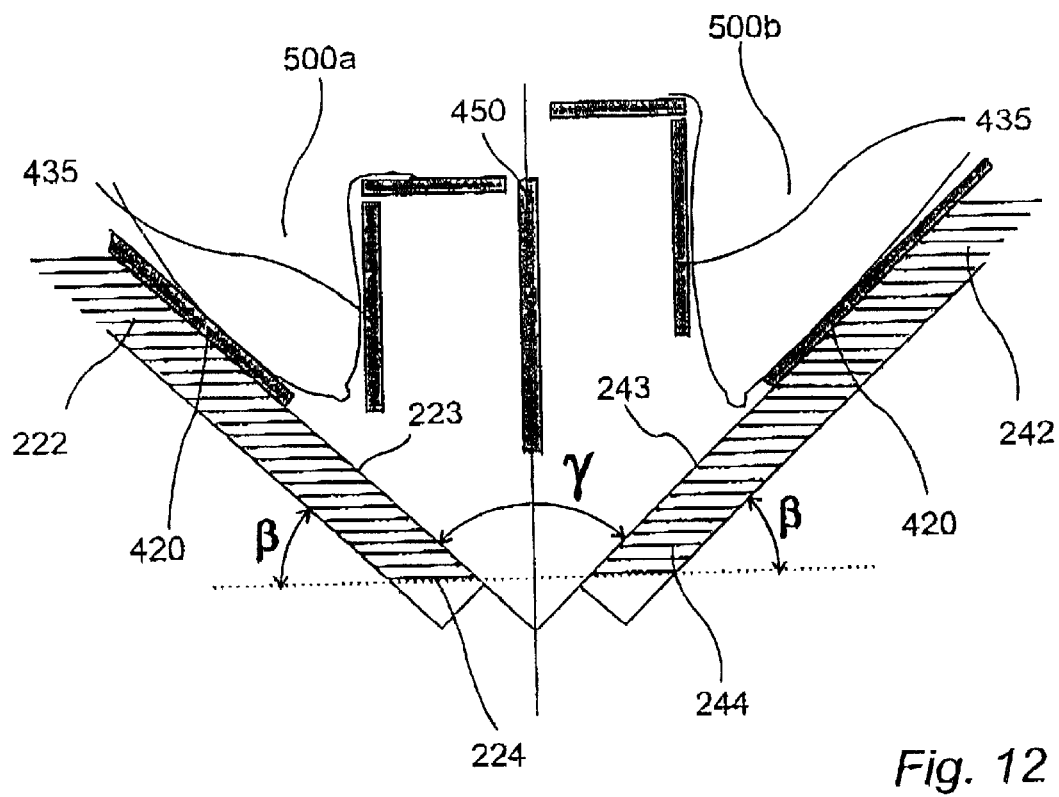
FIG. 12 is a partial sectional view of the camera for showing the configuration of the collimator holes.

FIG. 11 shows a sectional view of the camera 200 with the breasts 500a and 500b of the patient accommodated for taking mammograms. Referring to FIGS. 7 and 11, the configuration of the camera 200 will be described below. As noted above, the camera 200 comprises a first scintillation camera 220 and a second scintillation camera 240. The first and second scintillation cameras 220 and 240 have first and second collimators 222 and 242, first and second scintillation crystals 224 and 244, and first and second arrays of photomultiplier tubes 226 and 246, respectively. The first collimator 222 defines a first camera surface 223 and a first field of view, and the second collimator 242 defines a second camera surface 243 and a second field of view. The first and second scintillation cameras 220 and 240 are fixed relative to each other such that they form a "V" shape, thereby allowing both breasts of the patient to be accommodated simultaneously during the production of mammograms or any treatment after mammography, resulting in significant time saving. It also allows for accommodation of all reasonable breast and body sizes of patients by way of the "V" shape of the camera 200. As illustrated in FIG. 12, the first and second camera surfaces 223 and 243, which are defined by the first and second collimators 222 and 242 respectively, form a "V" shape with a selected angle γ between them. This angle may be about 90 degrees as shown, but this angle can be varied substantially while still providing good results. Further details will be described hereafter in conjunction with the explanation of the breast holding mechanism 400 of the apparatus 100.

Referring back to FIG. 5, the bed structure 300 is provided with a mechanism 366 for angularly adjusting the patient platform 320 about a vertical axis relative to the camera 200 to permit the taking of three-dimensional images, as noted above. The angularly adjustment mechanism includes an elongated bar 366 inserted through the housing of the driving mechanism 360 and a rotating axis lock 367 provided at one end of the elongated bar 366 whereby to rotate the bar 366. The patient platform 320 is adjustably rotated about the vertical axis (Z-axis) passing through the rotating axis lock 367 by handling the other end of the elongated bar 366. As shown in FIG. 7, the camera 200 is provided with a rotating axis pin 265 in the support plate 260. As shown in FIG. 1, the rotating axis lock 367 can be engaged with the rotating axis pin 265, for example, by way of a female-male interconnection, so that the patient platform 320 can be rotated to either side by a selected certain degrees about the vertical Z-axis passing through the rotating axis lock 367 and the rotating axis pin 265 either by manually moving the other end of the elongated bar 366 or by providng an automatic driving mechanism. Further details concerning the adjustment procedure and mechanism will follow below.

Figure 9:
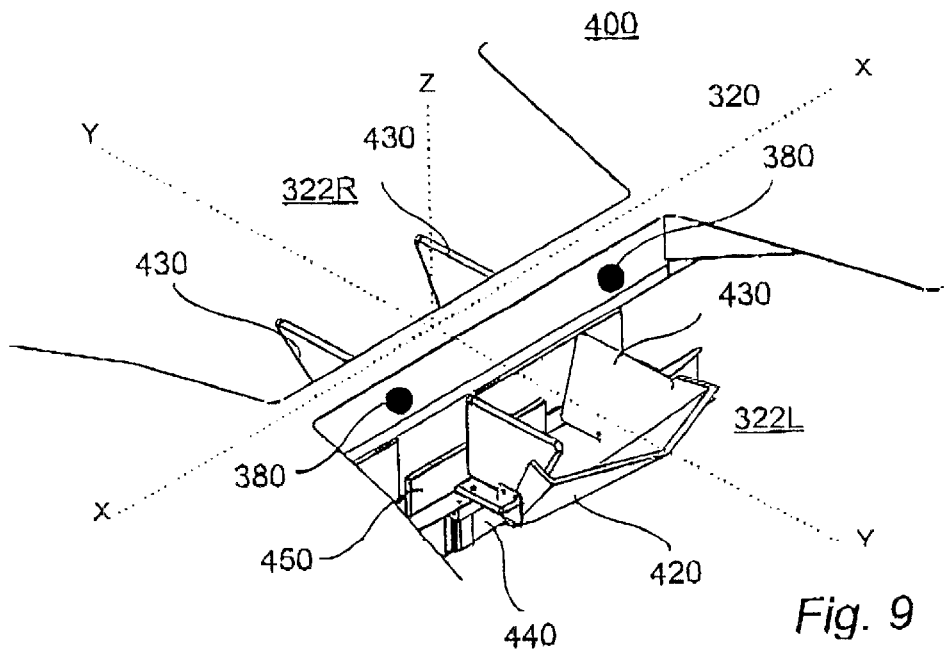
FIG. 9 is an enlarged perspective view of the breast holding mechanism in FIG. 5.

For the convenience of description, the X-axis, Y-axis, and X-axis in the drawings of the application and several necessary directions will be defined and be used with the same definitions and meanings throughout the application including the claims appended thereto. The X-axis corresponds to the longitudinal centre line of the platform 320. Therefore, when a patient lies face down on the platform 320, the X-axis is parallel to the longitudinal direction of the patients and passes the centre of the cleavage portion between her both breasts, as clearly depicted in FIG. 9. Hereinafter, a "longitudinal direction" refers to any direction parallel to the X-axis. The Y-axis normal to the X-axis corresponds to a transversal direction of the patient platform 320, and also passes transversally through the openings 322L and 322R of the platform 320 as shown in FIGS. 3 and 9. Therefore, the Y-axis passes through both breasts of the patient substantially along her chest wall when she lies face down on the platform 320. Hereinafter, a "transversal direction" refers to any direction parallel to the Y-axis. The Z-axis is defined by the direction normal to both of the X-axis and Y-axis and also passes the intersecting point of the X-and Y-axis, as clearly depicted in FIGS. 2 and 4. Hereinafter, a "vertical direction" refers to any direction parallel to the Z-axis.

Figure 8:
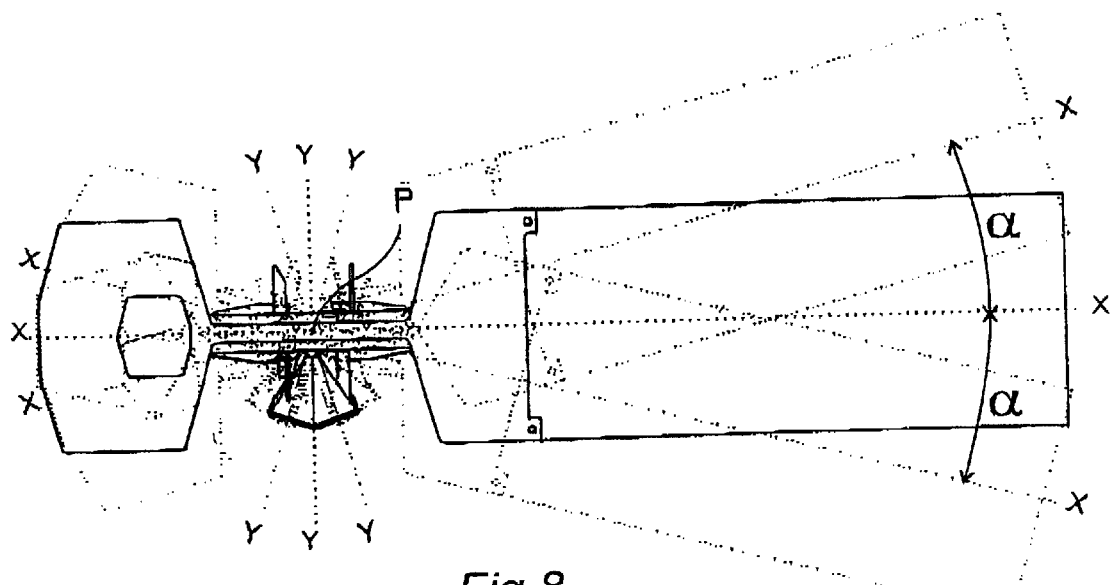
FIG. 8 shows the tilting operation of the bed structure and the breast holding mechanism.

According to these axes definitions, the angular adjustment axis of the patient platform 320 corresponds to the Z-axis passing through the intersection point P of the X-and Y-axis, as shown in FIG. 1. As illustrated in FIG. 8, the patient platform 320 can be rotated by a certain degree a to either side about the Z-axis passing the point P. Substantially, the angular adjustment axis passes through the central point of the cleavage area between both breasts of the patient who lies face down on the patient platform 320. Therefore, when the platform 320 is rotated to both sides alternatively about the angular adjustment axis, the breasts contained in the holding mechanism 400 also rotate clockwise and counterclockwise alternatively about the angular adjustment axis, allowing for three-dimensional imaging of both breasts at the same time. This aspect of the invention will be described below in greater detail in connection with the breast holding mechanism 400 of the apparatus 100.

Figure 10:
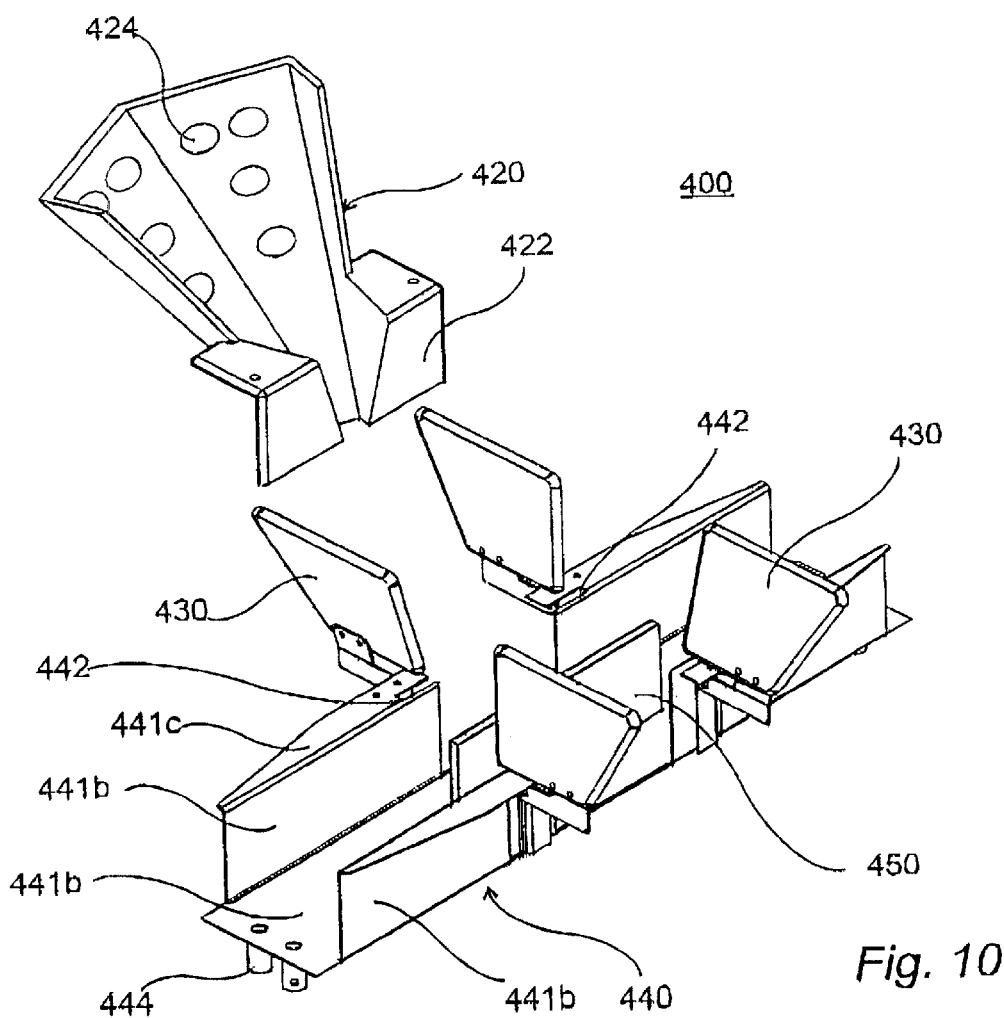
FIG. 10 is an exploded view of the breast holding mechanism.

Referring to FIGS. 9 and 10, the breast holding mechanism 400 will be described below. FIG. 9 shows an enlarged view of the breast holding mechanism 400 attached to the bed structure 300. The breast holding mechanism is detachably attached to the underside of the bed structure 300, and specifically to that area between the openings 322L and 322R of the patient platform 320. As depicted in FIG. 9, the mechanism 400 can accommodate both naked breasts of the patient, which hang down through the openings 322L and 322R when she lies face down on the patient platform 320 (after having been administered with a radiopharmaceutical.) The breast holding mechanism 400 is designed to fit into and to be accommodated into the shape of the V-shape camera 200. As illustrated in FIG. 11, when the breast holding mechanism 400 is fitted into the camera 200, the first scintillation camera 220 is associated with one of the breasts 500a and the second scintillation camera 240 with the other breast 500b, such that both breasts of the patient can be imaged or treated at the same time, leading to a significant time saving for everyone involved.

The apparatus illustrated herein is designed to cover the armpit area of a patient as well. As illustrated in FIGS. 4 and 11, when a patient lies face down on the patient platform 320 with the breasts being located within the breast holding mechanism 400, the armpit areas of the patient are also accessible i.e. within the field of view of the camera 200. Therefore, the camera can view and image the axillary lymph nodes in the armpit area to which the breast cancer or tumours can possibly spread first by way of the body's lymphatic system. It is essential to know whether cancer cells are present in these lymph nodes to determine how far the cancer has spread, i.e., to check the stage or level of cancer progression. Also, it is important to know the status of cancer progression to consider the choice and level of subsequent treatment after mammography.

As noted above, while rotating the patient platform 320 about the angular adjustment axis to either side, the breasts contained in the breast holding mechanism 400 must also rotate to the same angular amount so as to be viewed to the camera 200 at various different angles, so that three-dimensional images can be taken of the breasts and, therefore, the x, y, and z coordinates of any lesion can be determined with suitable image processing by the computer 280. As part of the three-dimensional image processing, the apparatus 100 is further provided with a radiation source 380 supported by or near the breast holding mechanism 400 (and in use near the cleavage area between the breasts) as shown in FIGS. 5 and 9. The radiation emitted by the source 380 is detected by the scintillation cameras 220 and 240 respectively, such that the relative position of the breasts to the camera can be determined while rotating the patient platform 320 about the angular adjustment axis. Then, by compensating the displacement of the breast position caused by the rotation with the relative position obtained above, the accurate x, y, z coordinates of a tumour or a cancer can be determined. These coordinates serve to guide a surgical tool or a biopsy gun to precisely access to the tumour or cancer site.

The radiation source 380 comprises an isotope emitting radiation, which has a different energy from that emitted by the radiopharmaceutical administered to the patient. The radiation emitted by the source 380 can be detected by the cameras 220 and 240, or in an alternate embodiment, a dedicated radiation detector (not shown) can be provided for sensing and processing the radiation emitted by the source 380.

FIG. 10 depicts an exploded view of the breast holding mechanism 400 detached from the bed structure 300. The breast holding mechanism 400 generally comprises a breast container 420 and a container support 440. The breast container 420 has the shape of an inverted half-cone sectioned through the vertical axis thereof (preferably the shape of an inverted truncated half-cone.) It can also have the shape of a chute flaring upward, as actually shown in FIG. 10. The above-noted shapes of breast container allow the breasts of women to be accepted regardless of their size. The breast container 420 is provided at the lower side thereof with a flange 422, which is snap-fitted into a slot 442 formed at the container support 440 for assembly therewith. As shown in FIG. 11, when the breast containers 420 accommodate the breasts, the inner surfaces of each breast container 420 touches the outer side of the breast and gently holds it without giving any pain to the patient. The outer surfaces of the two containers 420 are in close proximity with the camera surfaces 223 and 243 respectively, while at the same time relative rotation between the containers 420 and camera surfaces 223 and 243 is permitted.

The breast container 420 is also provided with a plurality of holes in the sidewall thereof, such that a surgical tool or a biopsy gun may have access to the breasts, subsequently to the mammography procedure. For example, in the case that a tumour or caner cell is found and the x, y, and z coordinates of the location thereof are determined, a surgical tool or a biopsy gun can have access to the breast through the holes 424 and be guided according to the x, y, z location coordinates.

The container support 440 comprises an elongated bottom wall 441a running along the longitudinal direction and a pair of parallel sidewalls 441b extending normal to the bottom wall along its longitudinal edges. Part of the sidewall is cut out at the middle thereof to accept the breast container 420 and so as not to interfere with the breast contained therein when in use. An elongated flange 441c is formed at and along and outwardly of the upper edge of the sidewall 441b. As illustrated in FIG. 10, the slots 442 to accept the flanges 422 of the breast containers 420 are formed in the elongated flanges 441c of the container support 440.

Referring to FIGS. 9 and 10, the breast holding mechanism 400 is further provided with spaced pairs of pushing pads 430 attached to the container support 440 so that the pads 430 gently push the upper and lower sides of the breasts to further hold the breasts and fit them into the breast containers 420. Similarly, the mechanism 400 includes further pushing pads 435 for gently pushing against the inner sides of the breasts as shown in FIG. 11. The pushing pads 435 are attached to the patient platform 320 of the bed structure. The breast container 420 and the pushing pads 430 and 435 are made of a suitable plastic material.

Therefore, the breasts are not firmly compressed as they are with conventional x-ray mammography, which can be painful, even days later. The apparatus 100 described herein gently holds the breasts with the purpose of keeping them as still as possible. As depicted in FIGS. 11 and 12, the breast is contained in the holding mechanism 400 without substantially distorting the inherent shape of breast. In other words, for the patient, the sensation will be like having the breasts gently placed into a plastic cup with only slight pressure.

The breast holding mechanism 400 is further provided with a pair of sleeves 444 at the bottom wall 441a of the container support 440. By way of the sleeves 444, the mechanism 400 is slidably attached to the bed structure 300, such that the relative distance between the mechanism 400 and the patient platform 320 can be changed by adjusting the height of the bed structure 300 and fixed at a suitable position for taking mammograms, depending on the size and shape of the breast. As illustrated in FIGS. 11 and 12, in case of a small breast 500a, the patient platform 320 is lowered together with the pushing pad 435, and in case of a large breast 500b, the platform 320 is raised to comfortably hold it. Therefore, with the cooperation of the height adjustment of the bed structure 300, the shape of the breast container 420, the pushing pads 430 and 435, and the slidable attachment of the breast holding mechanism, etc., the apparatus 100 as described gently and comfortably accommodate and image the breasts, regardless of the size, shape and hardness thereof.

Further, the apparatus 100 includes a shielding plate 450 positioned, in use, between both breasts of the patient, as depicted in FIGS. 10 to 12. The shielding plate 450 serves to shield radiations emitted from both breasts and, therefore prevent any cross-talk between the first and second scintillation cameras 220 and 240. In this embodiment, the shield plate 450 is attached vertically to the bottom wall 441a of the container support. However, it can be provided at any location suitable for shield the radiation from the opposing breast. The shielding plate 450 is made of lead.

FIG. 12 shows the configuration of collimator holes in the cameras 220 and 240. The collimators 222 and 242 have holes 224 and 244 slanted relative to the camera surfaces 223 and 243. With this configuration of collimator holes, any radiations from other body parts through the chest wall of the patient are prevented from being sensed by the camera. When a patient is administered with a radiopharmaceutical, the whole body emits radiation in all directions. In case of the breast study, a relatively large quantity of radiation is emitted by other neighboring organs through the chest wall as compared with those radiation emitted from the breasts, since their combined volume is much smaller than that of the other organs. Therefore, if the collimator holes were to be formed normal to the camera surface, part of the radiations from the chest wall would be sensed and processed by the cameras, leading to blurred images and unacceptable results. Therefore, as shown in FIG. 12 and noted above, the collimator holes 224 and 244 are slanted relative to the camera surfaces 223 and 243. In this embodiment, the collimator holes are parallel to the transverse direction of the patient platform 320, substantially parallel to the chest wall of the patient, such that the radiations from the breasts only enter through the collimator holes 223 and 243, while the radiations from the chest wall in any direction cannot enter into the collimator holes. In FIG. 12, the angle between the first and second scintillation cameras 220 and 240 is denoted by a reference character γ, and the angle between the collimator holes 224 and 244 and the camera surfaces 223 and 243 by β. In order for the collimator holes to be parallel to the transversal direction, substantially parallel to the chest wall of the patient, the angle β varies depending on the angle γ. For example, where the angle γ between the cameras is 90 degrees, the angle β is 45 degrees for the collimator holes to be parallel to the transversal direction of the patient platform, and thus substantially parallel to the chest wall of the patient.

While the present invention has been described with reference to specific embodiments, the description is illustrative of the invention and is not to be construed as limiting the invention. Various modifications may occur to those skilled in the art without departing from the true spirit and scope of the invention as defined by the appended claims.

What is claimed is:

1. An apparatus for mammography, the apparatus comprising:
   (a) a bed structure having a patient platform on which a patient lies face down, said patient platform having at least one opening through which the breasts of the patient hang down when in use;
   (b) a mechanism having a pair of breast containers for accommodating and holding the breasts which extend down through said opening in selected substantially fixed relation relative to said platform, said mechanism being adapted to accommodate the breasts without substantially distorting the inherent shape of the downwardly extending breasts; and
   (c) a camera for providing a mammographic image of the breasts as they are being held by said mechanism, said mechanism maintaining substantially the shape of said breasts in the field of view of the camera.

2. An apparatus according to claim 1, wherein said camera is adapted to receive radiant energy from the patient breasts after the patient has been administered with a radiopharmaceutical substance, while substantially reducing the amount of radiation received by the camera from the remainder of the patient's body.

3. An apparatus according to claim 2, wherein said camera comprising:
   (a) a first scintillation camera having a first collimator, said first collimator defining a first camera surface;
   (b) a second scintillation camera having a second collimator, said second collimator defining a second camera surface;
   (c) wherein said first and second scintillation cameras are fixed relative to each other such that said first and second camera surfaces together form a "V" shape; and
   (d) said pair of breast containers being located between said first and second scintillation cameras and within the confines of the "V" shape, thereby allowing mammographic images of both breasts of the patient to be provided simultaneously.

4. An apparatus according to claim 3, further comprising means for shielding radiation from each other breast.

5. An apparatus according to claim 4, wherein said shielding means is located to prevent a cross-talk between said first and second scintillation cameras.

6. An apparatus according to claim 3, wherein the collimator holes of said collimators are slanted relative to the camera surfaces such that radiation from other body parts of the patient is substantially prevented from being received by scintillation cameras.

7. An apparatus according to claim 6, wherein the slant holes in said collimator holes are parallel to the transversal direction of said patient platform, and thus substantially parallel to the chest wall of the patient when lying face down on said patient platform.

8. An apparatus according to claim 6, wherein said first and second camera surfaces are at about 90 degrees with each other, and the collimator holes are at about 46 degrees with said camera surfaces.

9. An apparatus according to claim 4, wherein said patient platform is rotatable about an axis normal to said platform and passing through a region intermediate said pair of breast containers whereby mammographic images of the breasts may be taken with said platform in different angular locations about said axis.

10. An apparatus according to claim 3, wherein said camera is accessible to the armpit area of the patient such that the axillary lymph nodes can be viewed by said camera.

11. An apparatus according to claim 1, wherein said bed structure is provided with an aperture for resting the face of said patient.

12. An apparatus according to claim 11, wherein said bed structure is provided with means, under said aperture, for distracting said patient from mammography.

13. An apparatus according to claim 12, wherein said distracting means includes an artistic picture.

14. An apparatus for mammography, the apparatus comprising:
   (a) a bed structure having a patient platform on which a patient lies face down, said patient platform having at least one opening through which the breasts of the patient hang down when in use;
   (b) a mechanism for holding the breasts which extend down through said opening in selected substantially fixed relation relative to said platform, said mechanism including a pair of breast containers for accommodating said breasts while maintaining substantially the shape of said breasts in the field of view of the camera:
   (c) a camera for providing a mammographic image of the breasts as they are being held by said mechanism; and
   (d) wherein said patient platform is rotatable about an axis normal to said platform and passing through a region intermediate said pair of breast containers whereby mammographic images of the breasts may be taken with said platform in different angular locations about said axis.

15. An apparatus according to claim 14, wherein said breast container has the shape of an inverted half-cone sectioned vertically through the vertex thereof.

16. An apparatus according to claim 14, wherein said breast container has the shape of a flaring chute.

17. An apparatus according to claim 14, wherein said breast holding mechanism further includes a pushing pad for further holding the breast and fitting it into the breast container.

18. An apparatus according to claim 17, wherein said pushing pad is made of a plastic material.

19. An apparatus according to claim 14, wherein said breast container is perforated so that a surgical tool or a biopsy gun is accessible to the breast therethrough.

20. An apparatus according to claim 14, wherein said breast holding mechanism is slidably and detachably attached to said bed structure.

21. An apparatus according to claim 14, wherein the distance between said breast holding mechanism and the bed structure can be adjusted depending on the size of the breasts of said patient.

22. An apparatus according to claim 14, wherein said bed structure further comprises means for adjusting the height thereof.

23. An apparatus for mammography, the apparatus comprising:
(a) a bed structure having a patient platform on which a patient lies face down, said patient platform having at least one opening through which the breasts of the patient hang down when in use;
(b) a mechanism for holding the breasts which extend down through said opening in selected substantially fixed relation relative to said platform;
(c) a camera for providing a mammographic image of the breasts as they are being held by said mechanism; and
(d) means for rotating said patient platform relative to said camera.

24. An apparatus according to claim 23, wherein said bed structure is rotated about a vertical axis passing through the cleavage area between of both breasts of the patient.

25. A patient supporting structure for using in the examination and treatment of women's breasts, the structure comprising:
(a) a bed structure having a patient platform on which a patient lies face down, said patient platform having an opening through which the breasts of said patient hang down; and
(b) a mechanism having a pair of breast containers for accommodating and holding the breasts hanging down through said opening, said mechanism being adapted to accommodate the breasts without substantially distorting the inherent shapes of the downwardly extending breasts, and to maintain substantially the shape of said breasts in the field of view of a camera.

26. A patient supporting structure according to claim 25, wherein said breast holding mechanism is slidably and detachably attached to said bed structure.

27. A patient supporting structure according to claim 25, wherein said breast holding mechanism includes a breast container for accommodating the breasts of the patient while maintaining substantially the shape of said breasts.

28. A patient supporting structure according to claim 27, wherein said breast container is made of a plastic material.

29. A patient supporting structure according to claim 27, wherein said breast container has the shape of an inverted half-cone sectioned vertically through the vertex thereof, preferably the shape of an inverted truncated half-cone sectioned vertically through the vertex thereof.

30. A patient supporting structure according to claim 27, wherein said breast container has the shape of a flaring chute.

31. A patient supporting structure according to claim 27, wherein said breast holding mechanism further includes a pushing pad for further holding the breast and fitting it into the breast container.

32. A patient supporting structure according to claim 31, wherein said pushing pad is made of a plastic material.

33. A patient supporting structure according to claim 27, wherein said breast container is perforated so that a surgical tool or a biopsy gun is accessible to the breast therethrough.

34. A patient supporting structure according to claim 25, wherein the distance between said breast holding mechanism and the bed structure can be adjusted depending on the size of the breasts of said patient.

35. A patient supporting structure according to claim 25, wherein said bed structure further comprises means for adjusting the height thereof.

36. A patient supporting structure according to claim 25, wherein said bed structure is provided with an aperture for resting the face of said patient.

37. A patient supporting structure according to claim 36, wherein said bed structure is provided with means, under said aperture, for distracting said patient from the examination and treatment.

38. A patient supporting structure according to claim 37, wherein said distracting means includes an artistic picture.

39. A patient supporting structure for using in the examination and treatment of women's breast, the structure comprising:
(a) a bed structure having a patient platform on which a patient lies face down, said patient platform having an opening through which the breast of said patient hangs down;
(b) a mechanism for holding the breast hanging down through said opening; and
(c) means for rotating said patient platform to both sides thereof.

40. A patient supporting structure according to claim 39, wherein said bed structure is rotated about a vertical axis passing through the cleavage area between of both breasts of the patient.

* * * * *

UNITED STATES PATENT AND TRADEMARK OFFICE
CERTIFICATE OF CORRECTION

PATENT NO. : 6,560,310 B2  Page 1 of 1
DATED : May 6, 2003
INVENTOR(S) : Iain Stark It is certified that error appears in the above-identified patent and that said Letters Patent is hereby corrected as shown below:

Column 2,
Line 33, please delete "collimnator", and insert therefor -- collimator --.
Line 35, please delete "ant", and insert therefor -- and --.

Column 3,
Line 40, please delete "ties", and insert therefor -- lies --.

Column 5,
Line 53, please delete "patients", and insert therefor -- patient --.

Column 6,
Line 5, please delete "a", and insert therefor -- α --.

Column 10,
Line 6, please delete "46", and insert therefor -- 45 --.

Signed and Sealed this

Sixteenth Day of December, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,560,310 B2
DATED : May 6, 2003
INVENTOR(S) : Iain Stark

It is certified that error appears in the above-identified patent and that said Letters Patent is hereby corrected as shown below:

Column 2,
Line 33, please delete "collimnator", and insert therefor -- collimator --.
Line 35, please delete "ant", and insert therefor -- and --.

Column 3,
Line 40, please delete "ties", and insert therefor -- lies --.

Column 5,
Line 53, please delete "patients", and insert therefor -- patient --.

Column 6,
Line 5, please delete "a", and insert therefor -- α --.

Column 10,
Line 6, please delete "46", and insert therefor -- 45 --.
Line 8, please delete "4" and insert therefor -- 3 --.

This certificate supersedes Certificate of Correction issued December 16, 2003.

Signed and Sealed this

Thirtieth Day of March, 2004

JON W. DUDAS
*Acting Director of the United States Patent and Trademark Office*